United States Patent [19]

Knifton et al.

[11] Patent Number: 5,304,681
[45] Date of Patent: Apr. 19, 1994

[54] TERT-BUTYLAMINE SYNTHESIS OVER MONTMORILLONITE CLAYS

[75] Inventors: John F. Knifton; Neal J. Grice, both of Austin, Tex.

[73] Assignee: Texaco Chemical Company, White Plains, N.Y.

[21] Appl. No.: 894,841

[22] Filed: Nov. 22, 1991

Related U.S. Application Data

[62] Division of Ser. No. 561,408, Aug. 1, 1990, Pat. No. 5,107,027.

[51] Int. Cl.$^5$ ............................................. C07C 209/60
[52] U.S. Cl. ..................... 564/485; 502/208; 502/210; 502/211; 502/242; 502/254; 502/255; 502/263
[58] Field of Search ............... 564/485; 502/208, 210, 502/211, 242, 254, 255, 263

[56] References Cited

U.S. PATENT DOCUMENTS

| | | | |
|---|---|---|---|
| 2,162,913 | 12/1935 | Eversole et al. | 502/210 |
| 2,537,282 | 1/1951 | Schaad | 564/485 |
| 2,750,417 | 6/1956 | Closson et al. | 564/485 |
| 2,984,687 | 5/1961 | Esmay et al. | 564/485 |
| 3,969,274 | 7/1976 | Frampton | 502/254 |
| 4,146,574 | 3/1979 | Onoda et al. | 502/211 |
| 4,565,801 | 1/1986 | Shimizu et al. | 502/211 |
| 4,962,263 | 10/1990 | Hamilton, Jr. et al. | 502/210 |

*Primary Examiner*—Glennon H. Hollrah
*Assistant Examiner*—Scott C. Rand
*Attorney, Agent, or Firm*—James L. Bailey; Kenneth R. Priem; Cynthia L. Kendrick

[57] ABSTRACT

Disclosed is a method for preparation of alkylamines which comprises reacting ammonia and a monounsaturated olefin in the presence of a catalyst selected from the group consisting of:
a. Acid modified montmorillonite clays;
b. Heterogeneous catalysts comprising a fluorine-containing compound on an inert support; and
c. Heteropoly acids on an inert support.

10 Claims, 1 Drawing Sheet

TERT-BUTYLAMINE SYNTHESIS OVER MONTMORILLONITE CLAYS

This is a division of application Ser. No. 07/561,408, filed Aug. 1, 1990, now U.S. Pat. No. 5,107,027.

FIELD OF THE INVENTION

This invention relates to the synthesis of alkylamines. More particularly this invention relates to a novel method for the synthesis of alkylamines which comprises reacting ammonia with a monounsaturated or polyunsaturated olefin of 2 to 10 carbon atoms, or mixtures thereof, over a catalyst comprising an acidic montmorillonite clay at a temperature of about 200° C. to 400° C. and a pressure of less than 5000 psi. For example, ammonia can be reacted with isobutylene to produce t-butylamine. Surprisingly the isobutylene conversion level with montmorillonite acidic clay catalysts and the related catalysts reported herein, under optimum temperature conditions, approximates the thermodynamically calculated limit as reported in the literature.

BACKGROUND OF THE INVENTION

Lower aliphatic amines find applications as organic intermediates for the synthesis of drugs, but also as bactericides, herbicides, rubber accelerators, corrosion inhibitors, extraction agents in the production of penicillin, surface active agents, etc.

Previously morpholine has been used as a rubber accelerator in various processes. Recently in the art there has been a trend to use primary amines as alternatives for morpholine. It has been demonstrated that highly hindered primary amines such as t-butylamine are especially useful in this regard.

Methods of preparation of primary amines are known in the art. "Functionalisation of Alkenes: Catalytic Amination of Monoolefins", by J. J. Brunet et al., *J. Mol. Catal.*, 49 (1989) 235-259 presents a review of amination of monoolefins.

The most widespread method for producing lower aliphatic amines is a reaction first achieved by Sabatier, involving the reaction of ammonia and an alcohol. Catalysts which have been used for the Sabatier reaction include silica-alumina, binary transition metal oxides, various metal phosphates and, recently, zeolites. Processes involving the reaction of ammonia and alcohols produce water which has to be separated from the product amine. It would be very desirable in the art if amines could be manufactured directly from alkenes, because it would save at least one-step in commercial operations. However, the conclusion of this article is that no expedient process has emerged for the catalytic amination of alkenes with ammonia or amines except for reactions with ethylene.

The direct addition of ammonia to alkenes is thermodynamically feasible, at least for ethylene and propylene, and can be accomplished in two ways, either by activation of the olefinic bond by coordination on a metal complex, thus forming a new species which can undergo nucleophilic attack by activation of the amine, or by activation of the amine by making it either more electrophilic (via amino radicals) or more nucleophilic (via metal amides).

Activation of an olefin can be promoted by many transition metals, however generally none of the products are the result of a simple monoaddition of the nucleophile on the olefin.

Organic and inorganic derivatives of Pd, Pt, Rh, Ru, Os or Ir, preferably on a support such as $Al_2O_3$, have been used to add ammonia to $C_2$-$C_6$ alkenes, however the conversions and selectivities were apparently low (see U.S. Pat. No. 3,412,158).

The addition of secondary aliphatic amines, including dimethylamine, methylamine, n-butylethylamine, pyrrolidine, morpholine and piperidine to ethylene in the presence of homogeneous Rh- or Ir- based catalysts to produce tertiary amines was reported by D. R. Coulson in the early 70s, see U.S. Pat. No. 3,758,586. Primary amines and ammonia did not react with ethylene under these conditions.

Catalytic amination of alkenes with ruthenium or iron catalysts was disclosed in European Patent Application 39061 (1981) to D. M. Gardner and R. T. Clark, as well as in U.S. Pat. No. 4,454,321 (1984). Here, reasonable conversions and yields appear to be limited to the use of ethylene as the alkene.

Markovnikov-addition-type monoamines have been formed by vapor phase amination of monoolefins in the presence of alumino silicates, see U.S. Pat. No. 4,307,250 (1981) and U.S. Pat. No. 4,375,002 (1983) to J. O. H. Peterson et al. Highest activities were obtained with small to medium pore acidic zeolites such as H-eronite and H-clinoptilotite, which were more effective than standard Linde SK-500 zeolite, a rare earth-exchanged Y zeolite. In addition, these catalysts exhibit higher life at high temperature, thus decreasing the chance of ethylene polymerization and other side reactions. Further, stoichiometric excess of ammonia appeared to contribute to high selectivities to monoethylamine.

Similar zeolite catalysts have been used by others to effect ethylene amination to ethylamine. An article titled "Direct Amination of Ethylène by Zeolite Catalysis" by M. Deeba, M. E. Ford and T. A. Johnson, *J. Chem. Soc. Commun.*, 1987, 562, describes the formation of ethylamine by addition of ammonia to ethylene catalyzed by acidic zeolites such as H-Y, H-mordenite and H-erionite.

The characteristic which allows these zeolites to act as catalysts for ethylene amination results from the highly acidic nature of the proton-exchanged zeolites. The necessity of strongly acidic sites and, thus, of a protonated ethylene intermediate for catalytic amination is demonstrated by the negligible activity of the non-acidic, sodium ion-exchanged, offretite and Y-zeolites and the weakly acidic amorphous silica alumina. Again, a high selectivity was observed and was believed to be the result of a stoichiometric excess of ammonia, Ibid.

The same researchers reported further work in "Amination of Olefins by Zeolites" by Deeba et al., *Catalysis,* 1987, 221. H-offretite, H-erionite, H-clinoptilolite, H-Y, and rare earth-exchanged Y were employed to obtain selectivities to the corresponding amines as high as 97%. This work included the conversions of ethylene, propylene and isobutylene to the corresponding amines.

Isobutylene was selectively converted to isobutylamine with greater than 98% yield between 220° C. and 300° C. It was noted that there was no detectable conversion of isobutylene with small pore zeolites such as H-erionite or H-clinoptilolite.

The activity of the zeolites investigated was correlated to the number of strong acid sites as determined by ammonia TPD.

It is also indicated that the mechanism of olefin amination results from the high acidic nature of proton-exchanged zeolites, wherein ethylene and propylene are reversibly adsorbed by zeolites, probably by means of the formation of a pi complex between the surface hydroxy group and the olefin.

It was also concluded that conversion of ethylene required the highest temperatures and the strongest acid sites, while propylene formed a more stable cationic intermediate activated by somewhat weaker acid sites.

In the case of isobutylene amination by ammonia, calculated product distributions indicate amination is favored by low temperature, high pressure and high ammonia/isobutylene ratios. Deeba et al. also noted that the activity of the solid acid catalysts generally correlates with the number of strong acid sites, and that t-butylamine formation likely involves the formation of the tert-butyl cation (see "Heterogeneous Acid-Catalyzed Amination of Isobutene to tert-Butylamine", *J. Org Chem.*, 1988, 53, 4594–4596).

Modified zeolites have also been used for producing amines. In German Patent 3327-000A to BASF borosilicate or borogermanate zeolite catalysts were used for amine production.

In German Patent 3634-247C to BASF chromium-containing borosilicate or ferrosilicate zeolite catalysts were used.

Zeolite catalysts were also used for preparation of amines by V. Taglieber et al., Canadian Patent 1,218,677 (1987) to BASF. In this process ammonia and amines are mixed with the olefin and reacted from about 200 to 300 bar and about 250° to 350° C. The catalysts are zeolites of the pentasil type.

Furthermore, U.S. Pat. No. 4,302,603 (1981), to G. Pez, discloses that a substantial improvement is obtained when the direct reaction of a monoolefin with ammonia is homogeneously catalyzed in liquid ammonia by $CsNH_2$, $RbNH_2$ or mixtures which may also include $KNH_2$ or $NaNH_2$ at temperatures below the critical temperature of ammonia.

U.S. Pat. No. 4,483,757 (1984) to Gardner et al., discloses the use of light energy in the presence of specified ammonium halides, such as $NH_4I$ or bromide, as photopromoters for the addition of ammonia, primary or secondary amines to $C_2$-$C_{18}$ monoolefinic compounds. The cost of such a process would be prohibitively expensive for large scale production.

It is also known in the art to produce t-butylamine by Ritter Chemistry wherein isobutylene is reacted with HCN to produce butylformamide which is hydrolyzed to t-butylamine plus formic acid. However, the use of HCN is very hazardous.

It would be a distinct advance in the art if there were discovered a very active, long life catalyst for preparation of alkylamines by addition of ammonia to olefins which were less expensive than any discussed which have been used in the art. It would be especially desirable if the catalyst allowed for the continuous synthesis of t-butylamine at the thermodynamically calculated limit of isobutylene conversion. As mentioned isobutylamine is being used more often as a substitute for morpholine as a rubber accelerator and improved methods of preparation are of importance to those in the art.

SUMMARY OF THE INVENTION

In accordance with the foregoing, the novel method of this invention for production of alkylamines comprises reacting ammonia with a monounsaturated or polyunsaturated olefin having 2 to 10 carbon atoms, or mixtures thereof, in the presence of a catalyst selected from the group consisting of:
1. Acid modified montmorillonite clays;
2. Heterogeneous catalysts comprising a fluorine-containing compound on an inert support; and
3 Heteropoly acids on an inert support.

DETAILED DESCRIPTION OF THE INVENTION

Figure 1:
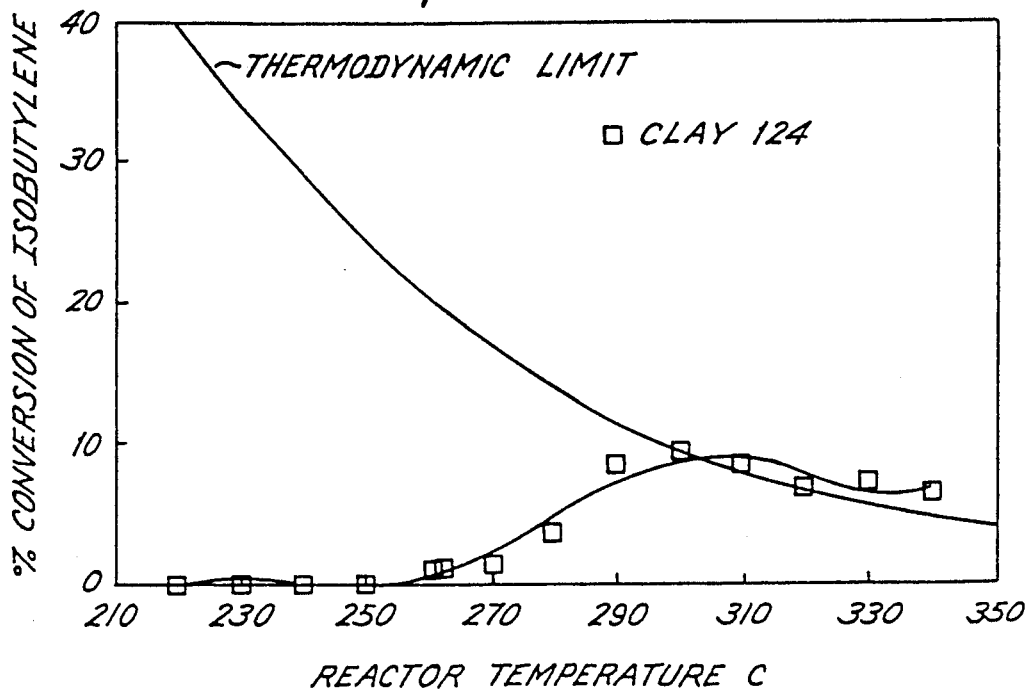
FIG. 1 summarizes analyses data for the operating temperature range from 220° to 340° C.

In the narrower and more preferred practice of this invention, ammonia is reacted with a monounsaturated olefin of 2 to 6 carbon atoms, or mixtures thereof, in the presence of a catalyst from the group consisting of:
1. An acidic montmorillonite clay;
2. Heterogeneous catalysts comprising a fluorine-containing compound on an inert support;
3. Heteropoly acids on titania at a temperature of 200° C. to 400° C. and pressure of atmospheric to 5000 psi.

The invention is particularly effective in the reaction of ammonia with isobutylene to synthesize tert-butylamine. This particular reaction can be represented by:

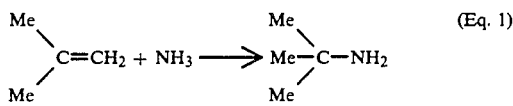

(Eq. 1)

Starting materials employed in the process are an olefin containing 2 to 10 carbon atoms and ammonia. The olefin is preferably an aliphatic linear, or branched-chain, monounsaturated olefin having from 2 to 6 carbon atoms per molecule, such as ethylene, propylene, isobutylene and isoamylene. The most preferred olefin is isobutylene.

Ammonia and the olefin are fed into a pressure reactor fitted with means of mixing in streams adjusted to maintain a mole ratio of ammonia to olefin of between 1:1 and 10:1. The reaction is maintained at a temperature of from 200° C. to 400° C. and a pressure of 0–5000 psig and the ammonia and olefin are passed over the catalyst producing as effluents alkylamines and unconverted ammonia and olefin. Typical samples of product effluent were collected in on-line bombs for one hour and analyzed by gas chromatography.

The catalyst systems suitable for the practice of this invention generally comprise acidic catalysts. At least three classes of acidic catalysts have been found effective for the desired production of alkylamines, such as isobutylamine, from the corresponding olefins. They include:
1) Acidic montmorillonite clays; including, but not limited to:
 a) layered montmorillonite clays that have been acidified by mineral acid treatment;

b) layered montmorillonite clays modified with certain Lewis acids;
c) layered montmorillonite clays modified with selected heteropoly acids;
d) layered montmorillonite clays modified with certain organic acids;

2) Heterogeneous catalysts comprising a fluorine-containing compound on an inert support; and 3) Heteropoly acids on an inert support.

1) Acidic Clays

A Variety of modified clays containing aluminum and silica are effective in the subject reaction (Eq. 1), however it is necessary that the alumina-silica matrix be acidic under normal operating conditions. A group of catalysts which works well in this synthesis are acidic clay mineral catalysts. Chemically clays are composed primarily of silicon, aluminum and oxygen, with minor amounts of magnesium and iron in some cases. Variations in the ratios of these constituents and their crystal lattice configurations result in some fifty separate clays, each with its own characteristic properties.

Particularly effective in the reaction of Equation 1 are smectite clays. Smectite clays are discussed in an article cited in Chem. Systems Report, 84-3, "Catalysis: Selective Developments," *Chem. Systems Report* 84-3, 239-249, at Section 3.4320. These clays have small particle size and unusual intercalation properties which afford them high surface area. They are aluminosilicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layered sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

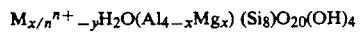

$$M_{x/n}{}^{n+} \cdot yH_2O(Al_{4-x}Mg_x)(Si_8)O_{20}(OH)_4$$

where M represents the interlamellar (balancing cation normally sodium or lithium and x, y and n are integers.

These montmorillonite clays are best used in the present application in an acidic form. Acids, particularly mineral acids such as sulfuric or phosphoric acids, activate montmorillonites by attacking and solubilizing structural cations in the octahedral layers. This opens up the clay structure and increases surface area. These acid-treated, particularly mineral acid treated, clays act as strong Bronsted acids.

Acid montmorillonite clays are the preferred form of smectite clay in the present invention. Preferably these acid clays should have acidities in the range of 3 to 20, or greater, mg KOH/gm, titrated to a phenolphthalein end point. Their surface area should be >30 m²/g and preferably 200 to 1000 m²/g. Their moisture content should be limited also, thereby upon heating to 220° F., the weight loss is generally less than 20 wt %.

Illustrative examples of suitable montmorillonite clays include powdered clays, such as Engelhard's Filtrol Grade 13, having a residual acidity of 15 KOH/gm, a surface area of 300 m²/g and a moisture content of 16 wt %, or Filtrol Grade 113, having a residual acidity of 10 mg KOH/gm, a surface area of 300 m²/g, and a moisture content of 4 wt %, as well as Filtrol Grade 160 having a residual acidity of 13 mg KOH/gm, a surface area of 330 m²/g, and a moisture of content of 15 wt %. Also suitable are clays in granular form, such as Filtrol Grade 24, having a 20-60 mesh size, an acidity of 16 mg KOH/gm, a surface area of 300 m²/g and a moisture content of 10 wt % and clay Grade 124 (20/60 mesh or powdered) having an acidity of 7.0 mg KOH/gm, a surface area of 400 m²/g, and a moisture content of 2%. Also effective are clays in extruded form, such as Clay-62 in 3/16" and 1/16" diameter extrudates. Said clays may be further dried in vacuo to <1% water content.

In another embodiment it has been surprisingly discovered that the generation of alkylamines by commercially available acidic montmorillonite clays such as those outlined above is improved significantly by modification of the clays with certain Lewis acids, such as a Group III or IV compound preferably from the group consisting of zirconium, titanium or aluminum.

The preparation of the zirconium, titanium or aluminum-modified clay catalyst is accomplished by treating an acidic montmorillonite clay, such as, for example Engelhard Clay-24 with an aqueous or alcoholic solution of the Group III or IV metal as a salt of an inorganic acid. For example granular montmorillonite clay can be added to an aqueous or alcoholic solution or suspension of zirconium(IV) chloride, titanium(IV) chloride or aluminum nitrate. Said salts may be partially hydrolyzed during this addition. Stirring is typically maintained for 1-2 days at about room temperature but this time period can be shorter. The mixture is then filtered, the solids washed until the washings no longer show detectable levels of metal ions and the final product dried in vacuo at 40° C.

In another embodiment heteropoly acids are used to modify the clays and act as Bronsted acids. The heteropoly acids comprise a class of acids formed by the condensation of two or more inorganic oxyacids; for example, phosphate and tungstate ions, when reacted in an acidic medium, are condensed to form 12-tungstophosphoric acid, a typical heteropoly acid (HPA) according to Equation 2:

$$PO_4^{3-} + 12WO_4^{2-} + 27H^+ \rightarrow H_3PW_{12}O_{40} + 12H_2O \quad \text{(Eq. 2)}$$

A wide variety of elements ranging from Group I to Group VIII can become the central atom of the HPA anion or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table A.

Anions containing the so-called Keggin structure have a condensation ratio of 1:12 and are the most typical of all HPA anions. Heteropoly acids with the Keggin structure and their homologues are generally the most readily available HPA's and the ones most commonly used in catalysis. The synthesis of these HPA's is well documented in the literature [see for example U.S. Pat. No. 3,947,323 (1976)]. The following are typical heteropoly molybdate anions:

TABLE 1

Typical heteropolymolybdate anions

| CONDENSATION RATIOS | HETERO ATOMS (X) | CHEMICAL FORMULAS |
|---|---|---|
| 1:12 Keggin structure | $P^{5+}, As^{5+}, Si^{4+}, Ge^{4+}$ | $[X^{n+}Mo_{12}O_{40}]^{-(8-n)}$ |
| Silverton structure | $Ce^{4+}, Th^{4+}$ | $[X^{4+}Mo_{12}O_{42}]^{8-}$ |
| 1:11 Keggin structure (decomposition) | $P^{5+}, As^{5+}, Ge^{4+}, Si^{4+}$ | $[X^{n+}Mo_{11}O_{39}]^{-(12-n)}$ |
| 2:18 Dawson structure | $P^{5+}, As^{5+}$ | $[X_2^{5+}Mo_{18}O_{62}]^{6-}$ |
| 1:19 Waugh structure | $Mn^{4+}, Ni^{4+}$ | $[X^{4+}Mo_9O_{32}]^{6-}$ |
| 1:6 Anderson structure | | |
| (A type) | $Te^{6+}, I^{7+}$ | $[X^{n+}Mo_6O_{24}]^{-(12-n)}$ |
| (B type) | $Co^{3+}, Al^{3+}, Cr^{3+}$ | $[X^{n+}Mo_6O_{24}H_6]^{-(6-n)}$ |
| 4:12 | $As^{5+}$ | $[H_4As_4Mo_{12}O_{52}]^{4-}$ |
| 2:5 | $P^{5+}$ | $[P_2Mo_5O_{23}]^{6-}$ |

The preferred heteropoly acids for the amination of isobutylene include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as their hydrates and the clay is added to the aqueous solution in granular form. Stirring is maintained for 1-2 days at room temperature. The mixture is then filtered, the solids washed with distilled water until the washings contain no detectable levels of heteropoly acid and the final product is dried in vacuo at 40° C.

In an additional embodiment, the montmorillonite clays may also be modified with certain organic acids, particularly fluorine-containing organic acids having the sulfonic acid functionality, such as trifluoromethanesulfonic acid.

2) Fluorine-Containing Supported Catalysts

Another acidic catalyst found suitable for amination of isobutylene is a heterogeneous catalyst comprising a fluorine-containing compound on an inert support. Particularly effective are fluorophosphoric acids and hydrogen fluoride, preferably on an inert, high surface area support, such as titania.

The fluorine impregnated on the catalyst in the instant invention can be present as a hydrogen fluoride group or fluorophosphoric acid group which is chemically bound to the titania support. In the latter case, the exact nature of the bonding is not fully understood, but is believed to include, for the fluorophosphoric acids-on-titania catalysts, the following:

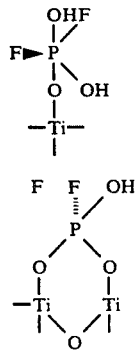

-continued

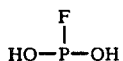

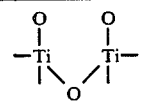

Said fluorine may be introduced onto the inert support as a fluorine-containing acid compound. The same fluorine may, for example, be introduced as a substituted phosphoric acid, such as a fluorophosphoric acid, including fluorophosphoric acid, $FPO_3H_2$ and difluorophosphoric acid $F_2PO_2H$. Also effective are acids such as hydrogen fluoride and aqueous hydrofluoric acid.

The support should preferably comprise an inert compound. Compounds which may be employed are those containing elements of Group III and IV of the Periodic Table. Suitable compounds include the oxides of aluminum, silicon, titanium and zirconium or combinations thereof, e.g. alumina, silica (silicon dioxide), titania (titanium dioxide) and zirconia, as well as combinations thereof. Also suitable are carbon, ion-exchange resins and carbon-containing supports. Good results were observed using $TiO_2$ as the support.

The inert support may be in the form of powders, pellets, spheres, shapes and extrudates. As will be demonstrated by the examples, the supports are preferably of high purity and high surface area. It has been found in the process of this invention that greater olefin conversion is achieved where the surface area of the support is generally >10 m²/g.

The reaction may be carried out in either a stirred slurry reactor or in a fixed bed continuous flow reactor. The catalyst concentration should be sufficient to provide the desired catalytic effect.

The weight percent of fluorine on the Group III/Group IV support should be such that the concentration of the fluorine-containing compound in the formulated catalyst is in the range of 0.1 wt % to 20 wt %, although concentrations outside this range may also be employed. Where the fluorine is, for example, difluorophosphoric acid, supported on titania, a suitable quantity of fluorine is 0.1-10 wt %.

3. Heteropoly Acid Supported Catalysts

A final type of catalyst which it has been discovered can be employed in olefin amination is a catalyst consisting of a heteropoly acid supported on an inert support. The heteropoly acids used in the catalyst of this embodiment are the same as those described above. Particularly effective are heteropoly acids such as tungstophosphoric, molybdophosphoric, tungstosilicic or molybdosilicic acid preferably on an inert, high surface area support. The reaction is carried out continuously and the catalyst preferably comprises a heteropoly acid on an inert, high surface area support, Group III or Group IV oxide, such as titania, alumina, silica, zirconia and combinations thereof. The catalysts are effective in the form of powders, granules or extrudates.

In the case of conversion of isobutylene to t-isobutylamine, suitable heteropoly acid catalysts may contain polyatoms selected from the group consisting of tungsten and molybdenum, while the heteroatoms may be phosphorous or silicon. These heteropoly acids would likely have the Keggin structure, $H_{8-n}[XM_{12}O_{40}]$, where X=P or Si, M=Mo or W and n is an integer which is 3 or 4.

During the synthesis of an alkylamine, or t-butylamine in particular, by reaction of ammonia and isobutylene the initial molar ratio of ammonia to alkylene is in the range of 1:1 to 10:1.

Generation of the alkylamines may be conducted batchwise, in a continuous slurry reactor, or in a fixed bed, continuous flow reactor. In all cases the catalyst concentration should be sufficient to provide the desired catalytic effect.

Synthesis of t-butylamine can generally be conducted at temperatures of 50° C. to 500° C.; the preferred range is 200° C. to 400°. The operating pressure may be from 0 psig to 5000 psig. The preferred range is 1500 to 3500 psig.

Typically the alkylamine is generated continuously in up to 10 wt % concentration in the crude product liquid. During continuous synthesis the isobutylene conversion level may reach at least 12% at 290° C. with t-butylamine the only significant product. The 12% conversion of isobutylene is close to the thermodynamic limit.

The yields are achieved at a total liquid hourly space velocity (LHSV) of 0.1 to 10 under mild conditions. LHSVs of 10 or greater have also been demonstrated to be useful in achieving the desired alkylene conversion. Here LHSV is defined as follows:

$$LHSV = \frac{\text{Weight of Total Liquid Feed Run Through the Reactor Per Hour}}{\text{Volume of Catalyst in Reactor}}$$

Conversion of isobutylene (wt %) is estimated in the following examples using the equation:

$$100 - \frac{\text{Wt \% Conc. of isobutylene in product \%}}{\text{Wt \% Conc. of isobutylene in Feed}} \times 100$$

Yields of t-butylamine are estimated from:

$$\frac{\text{Moles of t-butylamine in product}}{\text{Moles of isobutylene in feed}} \times 100$$

The attached examples illustrate:
1) The batch synthesis of t-butylamine via amination of isobutylene (NH$_3$:C$_4$H$_8$ initial ratio, 2:1) with Engelhard Grade 24 clay granules (Example 1).
2) The continuous synthesis of t-butylamine over another acidic montmorillonite clay (Engelhard Grade 124 clay powder), which at 300° C. operating temperature, gives (Example 2):
Isobutylene conversion of 9.5%
t-Butylamine concentration in the total effluent: 6.3%.
3) The continuous synthesis of t-butylamine at higher initial ammonia to isobutylene molar ratios of 4:1, where at 290° C. (Example 3):
Isobutylene conversion is 12.49%
t-Butylamine concentration in the total effluent: 4.6%.
4) The continuous synthesis of t-butylamine using fluorophosphoric acid-on-titania, trifluoromethanesulfonic acid-modified Clay 124, and 12-tungstophosphoric acid-on-titania catalysts (Examples 5–7).

These examples are only intended as a means of illustration and it should be understood that the invention is not limited thereby.

EXAMPLE 1

To a 183 ml pressure reactor fitted with means of mixing, temperature and pressure control, was charged 40.0 g of acidic montmorillonite clay (Engelhard Clay 24, Granules). Isobutylene (28 g, 0.5 mole) and ammonia (34 g, 2.0 mole) were each pressured into the reactor and the mixture heated to 250° C. slowly, with mixing, and held at temperature for 4 hours. Pressure in the reactor reached 3450 psi maximum.

Upon cooling to room temperature, two samples of the residual gas in the reactor were taken and analyzed by gas chromatography. Both samples showed the presence of tertiary butylamine.

EXAMPLE 2

To a 100c capacity, tubular, reactor system with temperature, pressure and flow controls, was charged about 65 g (98 ml) of acidic montmorillonite clay (Engelhard Clay 124, powder <80 mesh). A mixture of ammonia (24 g/hr) and isobutylene (40 g/hr) were fed continuously, upflow, to the reactor at a series of operating temperatures, while maintaining a total pressure of 2500 psi. Typical samples of product effluent were collected in on-line bombs for 1 hour and analyzed by gas chromatography.

Analyses data for the operating temperature range 220° to 340° C. are summarized in Table 1 and FIG. 1.

Typically, at an operating temperature of 300° C., the product effluent comprises:

| | |
|---|---|
| Isobutylene | 60.0% |
| Ammonia | 33.5% |
| t-Butylamine | 6.3% |

EXAMPLE 3

To a 100c capacity reactor system of Example 2 was charged the 65 g of Engelhard Grade 124 clay. A mixture of ammonia (24 g/hr) and isobutylene (20 g/hr) were fed continuously to the catalyst bed at a series of operating temperatures. Typical samples of product effluent were collected on-line for 1 hour and analyzed.

Figure 2:
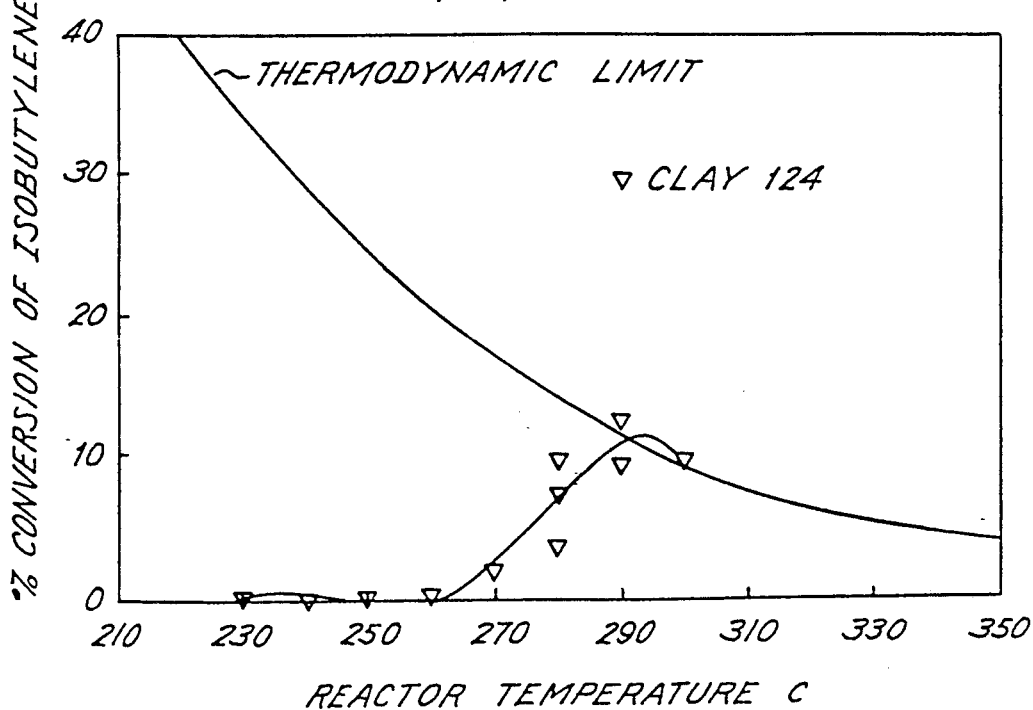
FIG. 2 summarizes analyses data for the operating temperature range from 230° to 280° C.

Data for these operating temperatures range from 230° C. to 280° C. and are summarized in Table 1 and FIG. 2.

Typically, at an operating temperature of 290° C., the product effluent comprises:

| | |
|---|---|
| Isobutylene | 32.5% |

-continued

| | |
|---|---|
| Ammonia | 62.5% |
| t-Butylamine | 4.6% |

EXAMPLE 4

To the 100c capacity reactor system of Example 2 was charged the 65 g of Engelhard Grade 124 clay. A mixture of ammonia (24 g/hr) and isobutylene (20 g/hr) were fed continuously to the catalyst bed at a series of operating temperatures. Typical samples of product effluent were collected on-line for 4 hours and analyzed.

Data for the operating temperature range 280° C. to 300° C. are summarized in Table 1.

TABLE 1
TERT-BUTYLAMINE SYNTHESIS
← % Conversion of Isobutylene to t-Butylamine →

| Operating Temp. (°C.) | Example 2 | Example 3 | Example 4 | Thermodynamic Limit[a] |
|---|---|---|---|---|
| 220 | 0 | | | |
| 230 | 0 | 0 | | 34 |
| 240 | 0 | 0 | | 29 |
| 250 | 0.12 | 0.16 | | 24 |
| 260 | 0.81 | 0.25 | | 21 |
| 262 | 1.14 | | | |
| 270 | 1.58 | 1.88 | | 17 |
| 280 | 3.79 | 3.56 | 9.71 | 14 |
| 290 | 8.53 | 12.49 | 9.14 | 11.5 |
| 300 | 9.50 | | 9.71 | 9.5 |
| 310 | 8.58 | | | 7.8 |
| 320 | 6.78 | | | 6.4 |
| 330 | 7.27 | | | 5.4 |
| 340 | 6.27 | | | 4.5 |

[a]Data taken from: M. Deeba and M. E. Ford, J. Org. Chem., 1988, 53,4594.

EXAMPLE A

To 300cc of titania (20/80 mesh) dried at 110° C. under vacuum, was added a solution of fluorophosphoric acid (26 g) in dried acetone (80cc) and the mixture stirred. The resulting mass was dried in vacuo at 50° C. for 1 hour then calcined at 150° C. for ½ hour in a flow of $N_2$ and finally at 350° C. for 2 hours flowing nitrogen.

The resulting catalysts was sieved to an 80 mesh screen.

EXAMPLE 5

To the 100cc capacity reactor system of Example 2 was charged 98cc of fluorophosphoric acid-on-titania catalyst, prepared by the method of Example A. A mixture of ammonia (24 g/hr) and isobutylene (40 g/hr) were fed continuously to the catalyst bed at a series of temperatures. Typical samples of product effluent were collected on-line for 1-2 hours and analyzed.

Data for the operating temperature range 320° to 340° C. are summarized in Table 2.

TABLE 2

| Operating Temp. (°C.) | % CONVERSION OF ISOBUTYLENE TO t-BUTYLAMINE |
|---|---|
| 320 | 0.5 |
| 330 | 2.2 |
| 340 | 1.0 |

EXAMPLE B

To a 100g of granular acidic clay (Filtrol Clay-124, dried to 0.4% $H_2O$ in vacuo), was added a solution of trifluoromethane sulfonic acid (5.0 g) in dried acetone (150cc). The mixture was stirred for 3-4 hours, filtered and the light tan solids washed with distilled water, then dried in vacuo at 40° C., overnight, then at 150° C. for 5 hours.

The resulting catalyst (62 g) was found to contain 0.05% S.

EXAMPLE 6

To the 100cc capacity reactor system of Example 2, was charged 98cc of trifluoromethanesulfonic acid treated Clay-124, prepared by the method of Example B. A mixture of ammonia (24 g/hr) and isobutylene (40 g/hr) were fed continuously to the catalyst bed at a series of temperatures. Typical samples of product effluent were collected on-line and analyzed.

Data for the operating temperature range 270° C. to 310° C. are summarized in Table 3.

TABLE 3

| Operating Temp. (°C.) | % CONVERSION OF ISOBUTYLENE TO t-BUTYLAMINE |
|---|---|
| 270 | 0 |
| 280 | 2.0 |
| 290 | 3.0 |
| 300 | 5.6 |
| 310 | 5.5 |

EXAMPLE C

To 250cc of titania extrudates (⅛" diameter, 51 $m^2/g$ surface area) was added a solution of 80.0 g of 12-tungstophosphoric acid in 150cc of distilled water. The mixture was stirred to absorb the liquid into the pores of the solid, excess liquid was removed by slow rotary evaporation, and the recovered white extrudates were calcined, first at 150° C. for 1 hour in a stream of nitrogen, then at 350° C. for 2 hours in a stream of nitrogen.

Analyses of the product catalyst shows the presence of:

| | |
|---|---|
| % W | = 15.8 |
| % P | = 0.31 |
| % $H_2O$ | = 0.72 |
| Acidity | = 20 mg KOH/g |

EXAMPLE 7

To the 100cc capacity reactor system of Example 2 was carried 98cc of the 12-tungstophosphoric acid-on-titania catalyst, prepared by the method of Example C. A mixture of ammonia (24 g/hr) and isobutylene (40 g/hr) were fed continuously to the catalyst bed at a series of temperatures. Typical samples of product effluent were collected on-line and analyzed.

t-Butylamine formation and isobutylene conversion were observed over the operating temperature range 250° to 300° C.

What is claimed is:

1. A method for preparation of alkylamines comprising reacting ammonia and a monounsaturated olefin containing 2 to 10 carbon atoms per molecule, in the presence of a catalyst comprising a heteropoly acid on an inert support.

2. The method of claim 1 wherein the olefin contains 2 to 6 carbon atoms.

3. The method of claim 1 wherein the olefin is isobutylene.

4. The method of claim 1 wherein temperature is from 200° C. to 400° C.

5. The method of claim 1 wherein the pressure is 0 psig to 5000 psig.

6. The method of claim 1 wherein the heteropoly acid is selected from the group consisting of 12-tungstophosphoric acid, 12-molybdophosphoric acid, 12-tungstosilicic acid and 12-molybdosilicic acid.

7. The method of claim 1 wherein the inert support is an oxide derivative of the elements of Group III and Group IV of the Periodic Table.

8. The method of claim 7 wherein the oxide support is selected from the group comprising alumina, silica, zirconia, titania, and combinations thereof.

9. The method of claim 8 wherein the support is titania.

10. The method of claim 1 wherein the catalyst is 12-tungstophosphoric acid-on-titania.

* * * * *